(12) United States Patent
Suita et al.

(10) Patent No.: US 9,955,874 B2
(45) Date of Patent: May 1, 2018

(54) PHANTOM

(71) Applicant: CANON KABUSHIKI KAISHA, Tokyo (JP)

(72) Inventors: Takahiro Suita, Kawasaki (JP); Ryo Ogawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 154 days.

(21) Appl. No.: 14/891,302

(22) PCT Filed: May 20, 2014

(86) PCT No.: PCT/JP2014/063764
§ 371 (c)(1),
(2) Date: Nov. 13, 2015

(87) PCT Pub. No.: WO2014/189147
PCT Pub. Date: Nov. 27, 2014

(65) Prior Publication Data
US 2016/0120412 A1    May 5, 2016

(30) Foreign Application Priority Data

May 23, 2013    (JP) ................................. 2013-108701

(51) Int. Cl.
*A61B 5/00*    (2006.01)
*A61B 8/00*    (2006.01)

(52) U.S. Cl.
CPC ............ *A61B 5/0095* (2013.01); *A61B 8/587* (2013.01); *A61B 2560/0223* (2013.01)

(58) Field of Classification Search
None
See application file for complete search history.

(56) References Cited

U.S. PATENT DOCUMENTS 5,799,059 A * 8/1998 Stembridge ............ A61B 6/583
378/18
6,694,047 B1 * 2/2004 Farrokhnia ............ A61B 6/583
378/163

(Continued)

FOREIGN PATENT DOCUMENTS

JP      2011-209691 A    10/2011
WO   2011/111572 A1    9/2011

OTHER PUBLICATIONS

Yin, G., et al., "Imaging of hemoglobin oxygen saturation using confocal photoacoustic system with three-optical-wavelength", Seventh International Conference on Photonics and Imaging in Biology and Medicine, 2009, pp. 72802E-72802E-8, vol. 7280.

(Continued)

*Primary Examiner* — Paul West
*Assistant Examiner* — Mark A Shabman
(74) *Attorney, Agent, or Firm* — Canon USA Inc., IP Division

(57) ABSTRACT

This invention provides a phantom whose light propagation characteristics and acoustic propagation characteristics are similar to those of human tissues and which allows detection of an absorber also with an ultrasonic wave diagnostic apparatus and allows adjustment of the oxygen saturation. A phantom has light absorbers 12*a* to 12*d* in a phantom base material 11, in which the light absorbers 12*a* to 12*d* approximate the light absorption coefficient ratio at two or more wavelengths to that of biological tissues, and the acoustic propagation characteristics of the phantom base material 11 and the light absorbers 12*a* to 12*d* are different from each other.

20 Claims, 4 Drawing Sheets

(56) References Cited

U.S. PATENT DOCUMENTS

2004/0245447 A1* 12/2004 Karasawa .............. A61B 6/583
  250/252.1
2014/0298886 A1* 10/2014 Nishi ................... A61B 5/0095
  73/1.86

OTHER PUBLICATIONS

Jiang, Y., et al., "Photoacoustic and Doppler Ultrasound for Oxygen Consumption Estimation: Implementation of a Clinical Array System", Photons Plus Ultrasound: Imaging and Sensing, 2011, pp. 1-6, vol. 7899, No. 1.

Cook, J., et al., "Tissue-mimicking phantoms for photoacoustic and ultrasonic imaging", Biomedical Optics Express, Nov. 1, 2011, pp. 3193-3206, vol. 2, No. 11.

Zhou, Y., et al., "Photoacoutsic microscopy of bilirubin in tissue phantoms", Journal of Biomedical Optics, Dec. 2012, vol. 17, No. 12.

* cited by examiner

PHANTOM

TECHNICAL FIELD

The present invention relates to a phantom and particularly relates to a phantom for use in accuracy control of a composite apparatus of a photoacoustic imaging system and an ultrasonic wave diagnostic apparatus.

BACKGROUND ART

The photoacoustic imaging system is an apparatus which displays an image based on detection signals of acoustic waves (typically ultrasonic waves) generated by thermal expansion of a measuring object when a living body serving as an examination object is irradiated with light. The diagnostic apparatus examines specific substances in the examination object, e.g., glucose, hemoglobin, and the like contained in blood.

It is known that when a tumor such as a cancer grows in biological tissues, blood vessels around the tumor are newly formed and the oxygen is increasingly consumed by the tumor. As a method of evaluating the formation of new blood vessels and the increase in oxygen consumption, the light absorption coefficient of oxyhemoglobin ($HbO_2$) and deoxyhemoglobin (Hb) can be utilized. For example, the photoacoustic imaging system measures the concentration of $HbO_2$ and Hb in blood from the light absorption coefficient of $HbO_2$ and Hb, respectively, at a plurality of wavelengths. Then, by creating a concentration distribution image of $HbO_2$ and Hb in the biological tissues, a region where the blood vessels are formed can be identified. Moreover, by calculating the oxygen saturation degree based on the light absorption coefficient ratio of $HbO_2$ and Hb at two or more wavelengths, a region where the oxygen consumption increases, which is considered to be a region where the tumor is present, can be identified. For example, it is known that the oxygen saturation in the tumor region reaches about 70%. Moreover, it is suggested that there is a correlation between the malignancy of the tumor and the oxygen saturation. When identifying the malignancy of the tumor using the oxygen saturation, the accuracy which allows identification of a difference of about 5% in the oxygen saturation is demanded.

Since it is difficult to recognize shape of the region with the photoacoustic imaging system, it is also difficult to distinguish signals based on a tumor from signals resulting from a noise and the like. Therefore, by combining the photoacoustic imaging system with an ultrasonic wave diagnostic apparatus, the identification of a tumor based on shape information can be achieved. To identify a tumor with the ultrasonic wave diagnostic apparatus, it is required to identify an acoustic impedance difference of about 0.1 rayl.

In a phantom for use in the photoacoustic imaging system, a material whose light propagation characteristics and acoustic propagation characteristics are similar to those of human tissues is demanded. For example, PTL 1 discloses a phantom for photoacoustic imaging system employing titanium oxide and polyol in which a carbon black pigment is dispersed.

CITATION LIST

Patent Literature

PTL 1 Japanese Patent Laid-Open No. 2011-209691

Technical Problem

The phantom for photoacoustic imaging system described in PTL 1 is a phantom containing, in a base material of a tissue equivalent agent containing polyol, a light absorber in which the dispersion amount of a carbon black pigment is adjusted based on the same polyol as that of the base material. The phantom for photoacoustic imaging system has a disadvantage in that it is difficult to recognize the shape of the light absorber because the acoustic propagation characteristics of the base material and the light absorber are almost the same.

The light absorber for use in the phantom for photoacoustic imaging system described in PTL 1 adjusts the absorption coefficient using one kind of pigment. Therefore, the absorption coefficients of $HbO_2$ and Hb at a plurality of wavelengths cannot be individually adjusted, so that the oxygen saturation cannot be varied.

Therefore, the present invention provides a phantom whose light propagation characteristics and acoustic propagation characteristics are similar to those of human tissues and which allows detection of a light absorber also with an ultrasonic wave diagnostic apparatus and allows adjustment of the oxygen saturation.

SUMMARY OF INVENTION

Solution to Problem

In order to solve the above-described disadvantages, the phantom of the present invention is characterized in that a light absorber is contained in a phantom base material, the light absorber approximates the light absorption coefficient ratio at two or more wavelengths to that of biological tissues, and the acoustic propagation characteristics of the phantom base material and the light absorber are different from each other.

Further features of the present invention will become apparent from the following description of exemplary embodiments with reference to the attached drawings.

Advantageous Effects of Invention

The present invention can achieve accuracy control of the oxygen saturation calculation which is functional information in a photoacoustic imaging system and can simultaneously achieve accuracy control of shape information in an ultrasonic wave diagnostic apparatus.

DESCRIPTION OF EMBODIMENT

Hereinafter, the present invention is described. The embodiment to be disclosed is one example of the present invention and the present invention is not limited thereto. In the present invention, "living bodies", such as a "human body", include not only a living body but a cut-out pathology site and the like.

The phantom of the present invention is formed by disposing a light absorber in a phantom base material and can perform accuracy control and calibration of a composite apparatus of a photoacoustic imaging system and an ultrasonic wave diagnostic apparatus.

The phantom base material and the light absorber suitably approximate the light propagation characteristics and the acoustic propagation characteristics to those of human tissues. As the light propagation characteristics, light scattering properties, light absorption properties, and the like are mentioned and the light propagation characteristics at a wavelength of 600 to 1100 nm are suitable. As the acoustic propagation characteristics, acoustic impedance, acoustic attenuation, and the like are mentioned and the acoustic propagation characteristics at a frequency of 0.5 to 10 MHz are suitable.

Figure 1:
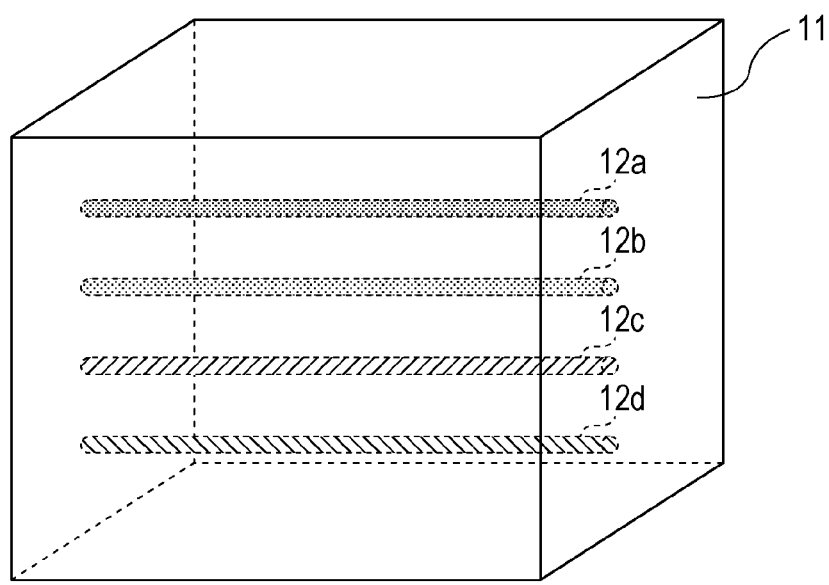
FIG. 1 is a schematic perspective view illustrating an example of a phantom of the present invention.

FIG. 1 illustrates one example of the phantom of the present invention. In this example, light absorbers 12a to 12d serving as detection objects of a mimic tumor and each having a different light absorption coefficient ratio are disposed in a phantom base material 11 in such a manner as to be able to be detected at the same depth position when disposing an apparatus. By the use of the phantom, the accuracy control of the oxygen saturation of the light absorbers disposed in the apparatus can be achieved. The size of the phantom illustrated in FIG. 1 is 120×120×50 mm and the size of the light absorbers 12a to 12d is 1 mm in diameter and 120 mm in length and the light absorbers are disposed in such a manner as to be able to be detected at a depth position of 25 mm when disposing the apparatus.

Figure 2:
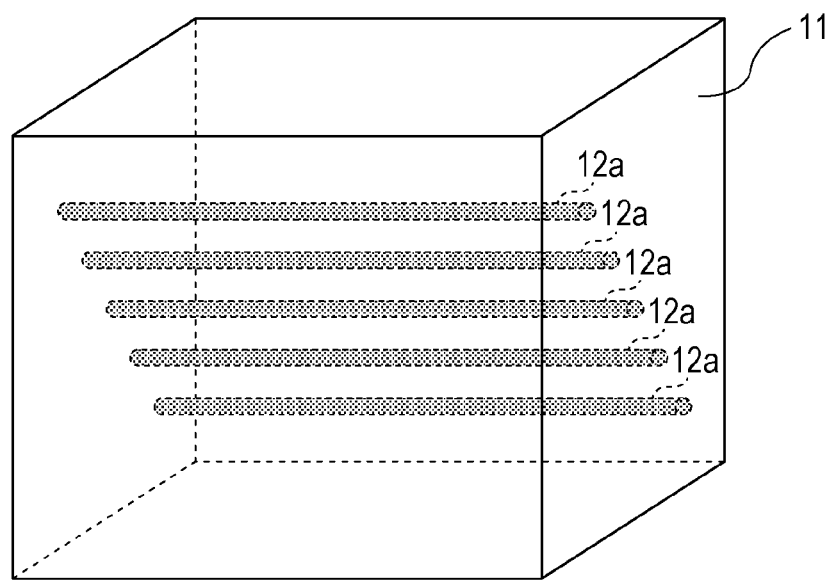
FIG. 2 is a schematic perspective view illustrating another example of the phantom of the present invention.

FIG. 2 illustrates another example of the phantom of the present invention. In this example, the light absorbers 12a serving as detection objects of a mimic tumor are disposed in the phantom base material 11 in such a manner as to be able to be detected at different depth positions when disposing an apparatus. By the use of the phantom, accuracy control of the depth dependence of the oxygen saturation of the light absorbers 12a disposed in the apparatus can be achieved. The size of the phantom illustrated in FIG. 2 is 120×120×50 mm and the size of the absorbers 12a is 1 mm in diameter and 120 mm in length and the absorbers 12a are disposed in such a manner as to be detected at depth positions of 5, 15, 25, 35, and 45 mm when disposing the apparatus.

Light Absorber

The light absorber of the present invention approximates the light absorption coefficient ratio at two or more wavelengths to that of biological tissues, suitably the light absorption coefficient ratio to that of hemoglobin. The light absorber of the present invention suitably contains two or more kinds of light absorbing compounds in the light absorber base material and more suitably contains two or more kinds of light absorbing compounds in the light absorber base material, in which the absorption coefficient ratios $\mu[\lambda_2]/\mu[\lambda_1]$ at arbitrary two wavelengths $\lambda_1$ and $\lambda_2$ ($\lambda_1 < \lambda_2$) of 600 nm or more and 1100 nm or less of the light absorbing compounds are different from each other and the parameter S calculated from the following equation (1) is 0 or more and 100 or less.

[Math. 1]

$$S = \frac{P' \cdot Hb[\lambda_1] - Hb[\lambda_2]}{(HbO_2[\lambda_2] - Hb[\lambda_2]) - P' \cdot (HbO_2[\lambda_1] - Hb[\lambda_1])} \cdot 100 \quad \text{Expression (1)}$$

$HbO_2[\lambda_1]$: Absorption coefficient of oxyhemoglobin at the wavelength $\lambda_1$
$HbO_2[\lambda_2]$: Absorption coefficient of oxyhemoglobin at the wavelength $\lambda_2$
$Hb[\lambda_1]$: Absorption coefficient of deoxyhemoglobin at the wavelength $\lambda_1$
$Hb[\lambda_2]$: Absorption coefficient of deoxyhemoglobin at the wavelength $\lambda_2$
P': Ratio ($P_{\lambda_2}/P_{\lambda_1}$) of the photoacoustic signal intensity $P_{\lambda_2}$ obtained by irradiation with light of the wavelength $\lambda_2$ to the photoacoustic signal intensity $P_{\lambda_1}$ obtained by irradiation with light of the wavelength $\lambda_1$ Light Absorber Base Material When the light absorbers are irradiated with light having a certain wavelength $\lambda$, the light absorbers thermally expands according to the absorption coefficient, so that acoustic waves (generally ultrasonic waves) are generated. Between the intensity P of the acoustic wave to be obtained, the intensity F of the laser light in that case, and the absorption coefficient $\mu$, the relationship of $P=\Gamma \cdot \mu \cdot F$ is established. $\Gamma$ is referred to as a Gruneisen coefficient and is a constant peculiar to materials.

In the light absorber base material of the present invention, the Gruneisen coefficient $\Gamma$ is important and is suitably similar to that of the living body. $\Gamma$ is suitably 0.1 or more and 2.0 or less. Since $\Gamma$ of biological soft tissues is around 1.0, $\Gamma$ is more suitably 0.5 or more and 1.5 or less.

In the present invention, the absorption coefficient of the light absorber can be adjusted by compounding a light absorbing compound in the light absorber base material. Therefore, as the light absorber base material simple substance, in the used wavelength band of the photoacoustic imaging system, the light absorption is suitably small and transparent.

Moreover, the Gruneisen coefficient $\Gamma$ has a relationship of $\Gamma=\beta \cdot v^2/C_p$ ($\beta$: Coefficient of cubic expansion, v: Acoustic velocity, $C_p$: Specific heat at constant pressure).

The coefficient of cubic expansion $\beta$ of the light absorber base material can be generally considered to be $\beta=3 \cdot \alpha$ ($\alpha$: Coefficient of linear expansion). The coefficient of linear expansion alpha of a general engineering plastic is 100 ppm/K or less. However, since the Gruneisen coefficient F becomes small in this case, the acoustic wave generated by light becomes weak, and thus it is not suitable as the light absorber base material. Therefore, the coefficient of linear expansion $\alpha$ of the light absorber base material is suitably 100 ppm/K or more and 1000 ppm/K or less and more suitably 200 ppm/K or more and 500 ppm/K or less from the viewpoint of the shape maintenance properties of the light absorber.

Since the acoustic velocity in biological tissues is in the range of about 1000 m/s to 1700 m/s, the acoustic velocity v of the light absorber base material is suitably 800 m/s or more and 2000 m/s or less and more suitably 1300 m/s or more and 1700 m/s or less particularly from the similarity of the acoustic propagation to soft tissues.

The specific heat at constant pressure $C_p$ of the light absorber base material is suitably in the range where the Gruneisen coefficient $\Gamma$ does not deviate from that of a living body according to the coefficient of linear expansion $\alpha$ because the specific heat of the biological soft tissues is 3.5 J/gK, which is greatly different from that of general materials.

As a material having such a physical property value, polymer materials, such as urethane resin, silicone resin, epoxy resin, acrylic resin, polyvinyl chloride, epoxy resin, polyethylene, nylon, natural rubber, polystyrene, and polybutadiene, can be mentioned but the material is not limited thereto. Among the above, a polyurethane gel which is one kind of a thermosetting urethane resin has an acoustic velocity v of about 1400 m/s, a coefficient of linear expansion $\alpha$ of about 300 ppm/K, and a Gruneisen coefficient $\Gamma$ of about 1.0 and is suitable as the light absorber base material of the present invention.

A curable polyurethane gel is typically obtained by reacting polyol and polyisocyanate but the invention is not limited thereto.

The polyol is not particularly limited insofar as it has two or more hydroxyl groups in the molecule and an arbitrary suitable polyol can be adopted. For example, polyester polyol, polyether polyol, polyacrylpolyol, polycarbonate polyol, and the like are mentioned. The use of the polyether polyol is more suitable in terms of the correlativity of the acoustic propagation characteristics of human tissues. The structure of the polyether polyol is suitably a copolymer having a molar ratio of ethylene oxide and propylene oxide in the range of 30:70 to 70:30 and having a number average molecular weight of about 5000 to 8000 from the correlativity of the acoustic propagation characteristics of human tissues and the stability of resin. These substances can be used singly or in combination of two or more kinds thereof.

The polyester polyol is typically obtained by reacting a polybasic acid component and a polyol component.

The polybasic acid component includes, for example, aromatic dicarboxylic acid, such as orthophthalic acid, isophthalic acid, terephthalic acid, 1,4-naphthalene dicarboxylic acid, 2,5-naphthalene dicarboxylic acid, 2,6-naphthalene dicarboxylic acid, biphenyl dicarboxylic acid, and tetrahydrophthalic acid; aliphatic dicarboxylic acid, such as oxalic acid, succinic acid, malonic acid, glutaric acid, adipic acid, pimelic acid, suberic acid, azelaic acid, sebacic acid, decane dicarboxylic acid, dodecane dicarboxylic acid, octadecane dicarboxylic acid, tartaric acid, alkyl succinic acid, linoleic acid, maleic acid, fumaric acid, mesaconic acid, citraconic acid, and itaconic acid; alicyclic dicarboxylic acid, such as hexahydrophthalic acid, tetrahydrophthalic acid, 1,3-cyclohexanedicarboxylic acid, and 1,4-cyclohexanedicarboxylic acid; or reactive derivatives, such as acid anhydrides thereof, alkyl ester, and acid halide, and the like. These substances can be used singly or in combination of two or more kinds thereof.

The polyol component includes ethylene glycol, 1,2-propane diol, 1,3-propane diol, 1,3-butane diol, 1,4-butane diol, neopentyl glycol, pentane diol, 1,6-hexane diol, 1,8-octane diol, 1,10-decane diol, 1-methyl-1,3-butylene glycol, 2-methyl-1,3-butylene glycol, 1-methyl-1,4-pentylene glycol, 2-methyl-1,4-pentylene glycol, 1,2-dimethyl-neopentyl glycol, 2,3-dimethyl-neopentyl glycol, 1-methyl-1,5-pentylene glycol, 2-methyl-1,5-pentylene glycol, 3-methyl-1,5-pentylene glycol, 1,2-dimethyl butylene glycol, 1,3-dimethyl butylene glycol, 2,3-dimethyl butylene glycol, 1,4-dimethyl butylene glycol, diethylene glycol, triethylene glycol, polyethylene glycol, dipropylene glycol, polypropylene glycol, 1,4-cyclohexanedimethanol, 1,4-cyclohexanediol, bisphenol A, bisphenol F, hydrogenated bisphenol A, hydrogenated bisphenol F, and the like. These substances can be used singly or in combination of two or more kinds thereof.

The polyether polyol is typically obtained by adding alkylene oxide to polyhydric alcohol by performing ring opening polymerization. The polyhydric alcohol includes, for example, ethylene glycol, diethylene glycol, propylene glycol, dipropylene glycol, glycerin, trimethylol propane, and the like. The alkylene oxide includes, for example, ethylene oxide, propylene oxide, butylene oxide, styrene oxide, tetrahydrofuran, and the like. These substances can be used singly or in combination of two or more kinds thereof.

The polyacrylpolyol is typically obtained by copolymerizing (meth)acrylate and a monomer having a hydroxyl group. The (meth)acrylate includes, for example, methyl (meth)acrylate, butyl(meth)acrylate, 2-ethylhexyl(meth)acrylate, cyclohexyl(meth)acrylate, and the like. The monomer having a hydroxyl group includes, for example, hydroxy alkyl ester of (meth)acrylic acid, such as 2-hydroxyethyl (meth)acrylate, 2-hydroxypropyl(meth)acrylate, 3-hydroxypropyl(meth)acrylate, 2-hydroxybutyl(meth)acrylate, 4-hydroxybutyl(meth)acrylate, and 2-hydroxypentyl(meth)acrylate; monoester(meth)acrylate of polyhydric alcohol, such as glycerin and trimethylol propane; N-methylol(meth)acryl amide; and the like. These substances can be used singly or in combination of two or more kinds thereof.

For the polyacrylpolyol, other monomers may be copolymerized in addition to the monomer component mentioned above. As other monomers, arbitrary suitable monomers can be adopted insofar as the monomers can be copolymerized. Specific examples of the monomers include unsaturated monocarboxylic acid, such as (meth)acrylic acid; unsaturated dicarboxylic acid, such as maleic acid and an anhydride thereof or mono or diesters thereof; unsaturated nitriles, such as (meth)acrylonitrile; unsaturated amides, such as (meth)acryl amide and N-methylol(meth)acryl amide; vinyl esters, such as vinyl acetate and vinyl propionate; vinyl ethers, such as methyl vinyl ether; $\alpha$-olefins, such as ethylene and propylene; halogenated $\alpha,\beta$-unsaturated aliphatic monomers, such as vinyl chloride and vinylidene chloride; $\alpha,\beta$-unsaturated aromatic monomer, such as styrene and $\alpha$-methylstyrene; and the like. These substances can be used singly or in combination of two or more kinds thereof.

The polyisocyanate includes, for example, aliphatic diisocyanates, such as tetramethylene diisocyanate, dodecamethylene diisocyanate, 1,4-butane diisocyanate, hexamethylene diisocyanate, 2,2,4-trimethylhexamethylene diisocyanate, 2,4,4-trimethylhexamethylene diisocyanate, lysine diisocyanate, 2-methylepentane-1,5-diisocyanate, and 3-methylepentane-1,5-diisocyanate; alicyclic diisocyanates, such as isophorone diisocyanate, hydrogenated xylylene diisocyanate, 4,4'-cyclohexylmethane diisocyanate, 1,4-cyclohexane diisocyanate, methylcyclohexylene diisocyanate, and 1,3-bis(isocyanatomethyl)cyclohexane; aromatic diisocyanates, such as tolylene diisocyanate, 2,2'-diphenylmethane diisocyanate, 2,4'-diphenylmethane diisocyanate, 4,4'-diphenylmethane diisocyanate, 4,4'-diphenyl dimethylmethane diisocyanate, 4,4'-dibenzyl diisocyanate, 1,5-naphthylene diisocyanate, xylylene diisocyanate, 1,3-phenylene diisocyanate, and 1,4-phenylene diisocyanate; and aromatic aliphatic diisocyanates, such as dialkyl diphenylmethane diisocyanate, tetraalkyl diphenylmethane diisocyanate, and $\alpha,\alpha,\alpha,\alpha$-tetramethylxylylene diisocyanate. These substances can be used singly or in combination of two or more kinds thereof.

The polyisocyanate can also be prepared as a denatured substance insofar as the effects of the present invention are not impaired. The polyisocyanate denatured substance includes, for example, multimers (dimers (for example, a uretdione denatured substance) and the like, trimmers (for example, an isocyanurate denatured substance and an iminooxadiazinedione denatured substance and the like) and the like), buret denatured substances (for example, a buret denatured substance generated by a reaction with water and the like), allophanate denatured substances (for example, allophanate denatured substances generated by a reaction with a mono-ol or low molecular weight polyol and the like), polyol denatured substances (for example, polyol denatured substance generated by a reaction with low molecular weight polyol or high molecular weight polyol and the like), oxadiazinetrion denatured substances (for example, oxadiazinetrion generated by a reaction with carbon dioxide), carbodiimide denatured substances (carbodiimide denatured substance generated by a decarbonization acid condensation reaction and the like), and the like but the invention not limited thereto.

Moreover, to the polyols or the polyisocyanates, a proper amount of a catalyst which promotes a reaction of a hydroxyl group of the polyol and an isocyanate group of the polyisocyanate may be added. As the catalyst, a known urethanization catalyst can be used. As a specific example of the catalyst, organometallic compounds, such as dibutyltin dilaurate, dibutyltin diacetate, and a dioctyltin dilaurate or organic amines, such as triethylene diamine and triethyl amine, and salts thereof are selected and used. These catalysts can be used singly or in combination of two or more kinds thereof.

Light Absorbing Compound

In order to approximate the light propagation characteristics of the light absorber to the light propagation characteristics of human tissues, the absorption coefficient is adjusted by dispersion of a light absorbing compound. The light absorbing compound suitably contains a combination of pigments in which the absorption coefficient ratio at two or more wavelengths can be adjusted in a near infrared region. It is suitable that the ratios $\mu[\lambda_2]/\mu[\lambda_1]$ at arbitrary two wavelengths $\lambda_1$ and $\lambda_2$ ($\lambda_1<\lambda_2$) of 600 nm or more and 1100 nm or less are different from each other.

In the light absorber of the present invention, a parameter S calculated from the following expression (1) can be controlled in the range of 0 or more and 100 or less by compounding two or more kinds of light absorbing compounds different in $\mu[\lambda_2]/\mu[\lambda_1]$.

[Math. 2]

$$S = \frac{P' \cdot Hb[\lambda_1] - Hb[\lambda_2]}{(HbO_2[\lambda_2] - Hb[\lambda_2]) - P' \cdot (HbO_2[\lambda_1] - Hb[\lambda_1])} \cdot 100 \quad \text{Expression (1)}$$

$HbO_2[\lambda_1]$: Absorption coefficient of oxyhemoglobin at the wavelength $\lambda_1$
$HbO_2[\lambda_2]$: Absorption coefficient of oxyhemoglobin at the wavelength $\lambda_2$
$Hb[\lambda_1]$: Absorption coefficient of deoxyhemoglobin at the wavelength $\lambda_1$
$Hb[\lambda_2]$: Absorption coefficient of deoxyhemoglobin at the wavelength $\lambda_2$
P': Ratio ($P_{\lambda_2}/P_{\lambda_1}$) of the photoacoustic signal intensity $P_{\lambda_2}$ obtained by irradiation with light of the wavelength $\lambda_2$ to the photoacoustic signal intensity $P_{\lambda_1}$ obtained by irradiation with light of the wavelength $\lambda_1$ The value of the absorption coefficient of oxyhemoglobin and deoxyhemoglobin at each wavelength can be obtained by the following method. More specifically, a solution in which oxyhemoglobin or deoxyhemoglobin is 100% can be prepared by adjusting the oxygen partial pressure in an aqueous solution containing hemoglobin of a certain fixed concentration. The absorption coefficient at each wavelength can be obtained by measuring the solution with a spectrum photometer.

Figure 3A:
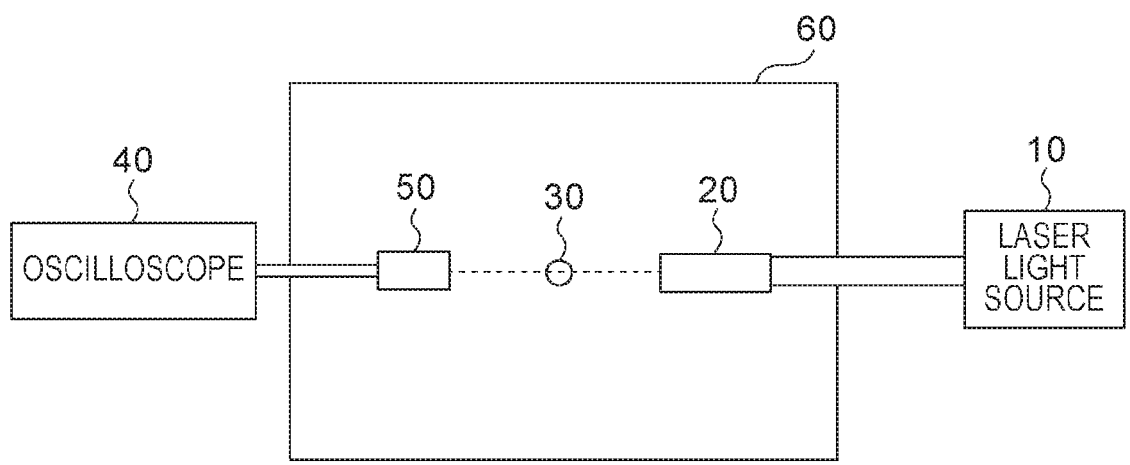
FIGS. 3A and 3B are views explaining a method for measuring the photoacoustic signal intensity.
Figure 3B:
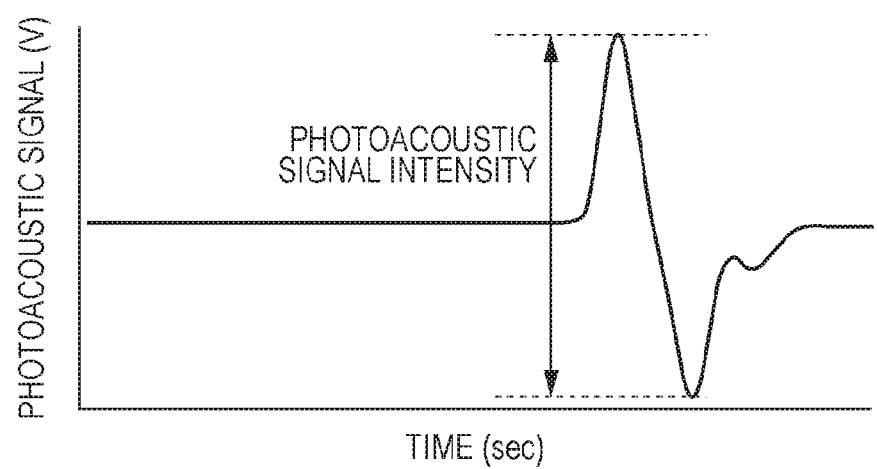

The photoacoustic signal intensity can be measured using a photoacoustic signal intensity measuring device illustrated in FIG. 3A. A test piece 30 is irradiated with laser light through an optical fiber 20 using titanium sapphire laser, for example, as a laser light source 10. As the test piece 30, a tube-like test piece is placed in a water tank 60 in such a manner as to cause no bending or the like. An acoustic wave generated by irradiating the test piece 30 with the laser light is received by an ultrasonic wave transducer which is a receiving device 50, and then the received voltage value of a photoacoustic signal received by the receiving device 50 is measured using an oscilloscope 40. The waveform of a typical photoacoustic signal is illustrated in FIG. 3B. The photoacoustic signal illustrated in FIG. 3B has a typical N-shaped waveform and the amplitude width of the maximum value and the minimum value is defined as the intensity of the photoacoustic signal.

The wavelength range of 600 nm or more and 1100 nm or less is a range referred to as a so-called "Biological window". The light having the wavelength in this range efficiently penetrates a human body and is suitable for use in a photoacoustic imaging system.

The parameter S is a value equivalent to the oxygen saturation of a human body. The light absorber of the present invention can imitate the oxygen saturation of a human body in photoacoustic wave diagnosis and is suitable for accuracy control and calibration of a photoacoustic imaging system.

Hereinafter, the respect that the light absorber of the present invention can control the parameter S calculated from Expression (1) in the range of 0 or more and 100 or less is described in detail.

First, the absorption coefficient at the wavelengths $\lambda_1$ and $\lambda_2$ of the light absorber can be arbitrarily adjusted by compounding two or more kinds of light absorbing compounds different in $\mu[\lambda_2]/\mu[\lambda_1]$ with an arbitrary ratio, and a parameter S' calculated from the following expression (1') can be adjusted.

[Math. 3]

$$S' = \frac{(\mu_a[\lambda_2]/\mu_a[\lambda_1]) \cdot Hb[\lambda_1] - Hb[\lambda_2]}{(HbO_2[\lambda_2] - Hb[\lambda_2]) - (\mu_a[\lambda_2]/\mu_a[\lambda_1]) \cdot (HbO_2[\lambda_1] - Hb[\lambda_1])} \cdot 100 \quad (1')$$

$HbO_2[\lambda_1]$: Absorption coefficient of oxyhemoglobin at the wavelength $\lambda_1$
$HbO_2[\lambda_2]$: Absorption coefficient of oxyhemoglobin at the wavelength $\lambda_2$
$Hb[\lambda_1]$: Absorption coefficient of deoxyhemoglobin at the wavelength $\lambda_1$
$Hb[\lambda_2]$: Absorption coefficient of deoxyhemoglobin at the wavelength $\lambda_2$
$\mu_a[\lambda_1]$: Absorption coefficient of the light absorber at the wavelength $\lambda_1$ $\mu_a[\lambda_2]$: Absorption coefficient of the light absorber at the wavelength $\lambda_2$ More specifically, the absorption coefficients of the light absorbing compounds A, B, C, . . . at the wavelengths $\lambda_1$ and $\lambda_2$ are defined as $\mu_A[\lambda_1]$, $\mu_B[\lambda_1]$, $\mu_C[\lambda_1]$ . . . and $\mu_A[\lambda_2]$, $\mu_B[\lambda_2]$, $\mu_C[\lambda_2]$ . . . , respectively. The content concentrations of the light absorbing compounds A, B, C . . . in the light absorbers are defined as $C_A$, $C_B$, $C_C$, . . . , respectively. Then, the following relationship is established between the absorption coefficient and the content concentration of the light absorbing compound and the absorption coefficients $\mu_a[\lambda_1]$ and $\mu_a[\lambda_2]$ of the light absorber:

$$\mu_a[\lambda_1] = C_A \cdot \mu_A[\lambda_1] + C_B \cdot \mu_B[\lambda_1] + C_C \cdot \lambda_C[\lambda_1] + \ldots,$$

$$\mu_a[\lambda_2] = C_A \cdot \mu_A[\lambda_2] + C_B \cdot \mu_B[\lambda_2] + C_C \cdot \lambda_C[\lambda_2] + \ldots.$$

When the absorption coefficient ratios $\mu_A[\lambda_2]/\mu_A[\lambda_1]$, $\mu_B[\lambda_2]/\mu_B[\lambda_1]$, $\mu_C[\lambda_2]/\mu_C[\lambda_1]$ . . . of the light absorbing compounds A, B, C, . . . are fixed, the absorption coefficient ratio $\mu_a[\lambda_2]/\mu_a[\lambda_1]$ of the light absorbing compounds is fixed, and therefore, the parameter S' cannot be controlled. Therefore, the absorption coefficient ratios at the wavelengths $\lambda_1$ and $\lambda_2$ of the light absorbing compounds A, B, C, . . . are required to be different from each other.

Therefore, by controlling the content concentration of the light absorbing compounds A, B, C, . . . in which the absorption coefficient ratios at the wavelengths $\lambda_1$ and $\lambda_2$ are different from each other in the light absorbers, the absorption coefficient ratio $\mu_a[\lambda_2]/\mu_a[\lambda_1]$ of the light absorber can be controlled. As a result, the parameter S' can be adjusted.

Herein, when the light absorbers are irradiated with light of the wavelengths $\lambda_1$ and $\lambda_2$, acoustic waves (generally ultrasonic waves) are generated because the light absorbers thermally expand according to the absorption coefficient. The relationship of $P_x = \Gamma \cdot \mu_x \cdot F_x$ is established between the intensity $P_x$ of the acoustic waves generated when irradiated with laser light of a certain wavelength x, the intensity $F_x$ of the laser light in that case, and the absorption coefficient $\mu_x$. $\Gamma$ is referred to as a Gruneisen coefficient and is a constant peculiar to materials. Therefore, when the intensity $F_x$ of the laser light is fixed, a proportionality relationship is established between the intensity $P_x$ of the acoustic wave and the absorption coefficient $\mu_x$. Therefore, the ratio P' ($P\lambda_2/P\lambda_1$) of the photoacoustic signal intensities $P\lambda_1$ and $P\lambda_2$ is the same value as $\mu_a[\lambda_2]/\mu_a[\lambda_1]$, and thus S'=S is established.

Therefore, by the use of two or more kinds of light absorbing compounds in which the absorption coefficient ratios at the wavelengths $\lambda_1$ and $\lambda_2$ are different from each other, the light absorber of the present invention can control the parameter S in Expression (1) in the range of 0 or more and 100 or less.

The light absorbing compound is a substance having light absorbability in a wavelength region of 600 nm or more and 1100 nm or less. The light absorbing compound is suitably a pigment from the viewpoint of weather resistance. However, in addition thereto, known colorants, such as dyes and pigments, can be used.

The light absorption characteristics of the light absorbing compound can be suitably selected based on the ratio of the absorption coefficients of oxyhemoglobin ($HbO_2$) and deoxyhemoglobin (Hb) at the wavelengths $\lambda_1$ and $\lambda_2$. More specifically, when the intensity $F_x$ of the laser light is fixed as described above, S'=S is established. Therefore, the absorption coefficient ratio $\mu_a[\lambda_2]/\mu_a[\lambda_1]$ of the light absorbers is defined as in the following expression based on Expression (1'):

$$\mu_a[\lambda_2]/\mu_a[\lambda_1] = ((S/100) \cdot HbO_2[\lambda_2] + (1-S/100) \cdot Hb[\lambda_2]) / ((S/100) \cdot HbO_2[\lambda_1] + (1-S/100) \cdot Hb[\lambda_1]).$$

In this case, when the parameter S is 0 or more and 100 or less, $\mu_a[\lambda_2]/\mu_a[\lambda_1]$ takes a value between $Hb[\lambda_2]/Hb[\lambda_1]$ and $HbO_2[\lambda_2]/HbO_2[\lambda_1]$. Therefore, the ratio $\mu_a[\lambda_2]/\mu_a[\lambda_1]$ of the absorption coefficient of the light absorber to be controlled is determined based on the value of the absorption coefficient of hemoglobin at a wavelength to be used. The light absorbing compound of the present invention can be selected as appropriate based on the absorption coefficient ratio of the hemoglobin.

According to the intended use of a photoacoustic imaging system, the ranges of the parameter S required for the light absorber varies. Therefore, when the lower limit of the parameter S is defined as $S_{min}$ and the upper limit of the parameter S is defined as $S_{max}$ according to the intended use of a diagnostic apparatus, it is suitable to contain at least one light absorbing compound in which the absorption coefficient ratio $\mu[\lambda_2]/\mu[\lambda_1]$ satisfies either one of the following expression (2) or expression (3). Furthermore, it is more suitable to contain at least one light absorbing compound in which the absorption coefficient ratio $\mu[\lambda_2]/\mu[\lambda_1]$ satisfies the other one of the following expression (2) or expression (3).

[Math. 4]

$$S_{min} \geq \frac{(\mu[\lambda_2]/\mu[\lambda_1]) \cdot Hb[\lambda_1] - Hb[\lambda_2]}{(HbO_2[\lambda_2] - Hb[\lambda_2]) - (\mu[\lambda_2]/\mu[\lambda_1]) \cdot (HbO_2[\lambda_1] - Hb[\lambda_1])} \cdot 100 \quad \text{Expression (2)}$$

$$S_{max} \leq \frac{(\mu[\lambda_2]/\mu[\lambda_1]) \cdot Hb[\lambda_1] - Hb[\lambda_2]}{(HbO_2[\lambda_2] - Hb[\lambda_2]) - (\mu[\lambda_2]/\mu[\lambda_1]) \cdot (HbO_2[\lambda_1] - Hb[\lambda_1])} \cdot 100 \quad \text{Expression (3)}$$

$S_{min}$: Lower limit of parameter S
$S_{max}$: Upper limit of parameter S
$HbO_2[\lambda_1]$: Absorption coefficient of oxyhemoglobin at the wavelength $\lambda_1$
$HbO_2[\lambda_2]$: Absorption coefficient of oxyhemoglobin at the wavelength $\lambda_2$
$Hb[\lambda_1]$: Absorption coefficient of deoxyhemoglobin at the wavelength $\lambda_1$
$Hb[\lambda_2]$: Absorption coefficient of deoxyhemoglobin at the wavelength $\lambda_2$
$\mu[\lambda_1]$: Absorption coefficient of the light absorbing compound at the wavelength $\lambda_1$
$\mu[\lambda_2]$: Absorption coefficient of the light absorbing compound at the wavelength $\lambda_2$ Hereinafter, the light absorbing compound is specifically described with reference to a case where light of $\lambda_1=756$ nm and light of $\lambda_2=797$ nm are used but the present invention is not limited thereto.

The absorption coefficient $Hb[\lambda_1]$ at 756 nm of deoxyhemoglobin is $1560.48 \times 10^{-6}$ mm$^{-1}$, the absorption coefficient $Hb[\lambda_2]$ at 797 nm is $792.66 \times 10^{-6}$ mm$^{-1}$, the absorption coefficient $HbO_2[\lambda_1]$ at 756 nm of oxyhemoglobin is $562.00 \times 10^{-6}$ mm$^{-1}$, and the absorption coefficient $HbO_2[\lambda_2]$ at 797 nm is $768.80 \times 10^{-6}$ mm$^{-1}$. Therefore, in order to set the parameter S of the light absorber in the range of 0 or more and 100 or less, the absorption coefficient ratio $\mu_a[\lambda_2]/\mu_a[\lambda_1]$ of the light absorber is required to be in the range of 0.51 or more and 1.37 or less range. Therefore, $\mu[\lambda_2]/\mu[\lambda_1]$ of one light absorbing compound is suitably 0.51 or less and $\mu[\lambda_2]/\mu[\lambda_1]$ of the other light absorbing compound is suitably 1.37 or more. A substance whose absorption coefficient ratio is not included in this range can be used for adjusting the absorption coefficient.

As a pigment having such an absorption characteristic, the following known pigments can be mentioned. Blue pigments include phthalocyanine pigments of phthalocyanine compounds substituted or not substituted by metal and the like and anthraquinone pigments. Red pigments include a monoazo pigment, a disazo pigment, an azo lake pigment, a benzimidazolone pigment, a perylene pigment, a diketopyrrolopyrrole pigment, a condensed azo pigment, an anthraquinone pigment, a quinacridone pigment, and the like. Green pigments include a phthalocyanine pigment, an anthraquinone pigment, and a perylene pigment similarly as in the blue pigments. Yellow pigments include a monoazo pigment, a disazo pigment, a condensed azo pigment, a benzimidazolone pigment, an isoindolinone pigment, an anthraquinone pigment, and the like. Furthermore, black pigments include Pigment Black 7, carbon black, and the like. In addition thereto, purple, orange, and brown pigments can also be used.

Among the above, a phthalocyanine compound, particularly a copper phthalocyanine which is a copper-substituted phthalocyanine compound, can be suitably used because $\mu[\lambda_2]/\mu[\lambda_1]$ is 0.51 or less and is close to 0, and therefore the controllability is good. The content of the phthalocyanine compound is not particularly limited and is suitably 0.000001% by weight or more and 0.1% by weight or less. Carbon black has $\mu[\lambda_2]/\mu[\lambda_1]$ of about 1 and can be suitably used for adjusting the absorption coefficient at each wavelength.

The light absorbing compound can be compounded by adding a mixture of a dispersing agent having affinity with the light absorbing compound, for example, a dispersing agent containing a polyol component, and the light absorbing compound to the light absorber base material. The dispersing agent having affinity with the light absorbing compound suitably has an anion group for improving the dispersibility of the light absorbing compound. As the anion group, a sulfonyl group and a carboxyl group are more suitably used. As the amount of the anion group, the anion group is suitably contained in such an amount that the anion group can disperse the light absorbing compound. Since the amount of the anion group affects the affinity to the light absorber base material, the amount is selected as appropriate according to the property of the light absorber base material. The polyol includes polyether polyol, polyester polyol, and the like, for example, and is selected as appropriate considering the affinity with the light absorber base material.

Light Scattering Compound

To the light absorber of the present invention, a light scattering compound may be added as appropriate, as required. The light scattering compound is added for approximation to the light propagation characteristics of human tissues and can adjust the equivalent scattering coefficient.

As the light scattering compound, inorganic particles can be suitably used. As the inorganic particles, inorganic particles having small absorption in the used wavelength band of a photoacoustic imaging system can be selected as appropriate. In order to scatter light, the refractive index is desirably different from that of the light absorber base material. In order to achieve scattering of the inorganic particles, the average particle diameter is suitably 0.1 μm or more and 0.3 μm or less and more suitably 0.2 μm or more and 0.3 μm or less. Such inorganic particles suitably contain silicon oxide, metal oxide, a composite metal oxide, a metallic compound semiconductor, metal, or diamond. Examples of the metal oxide include aluminum oxide, titanium oxide, niobium oxide, tantalum oxide, zirconium dioxide, zinc oxide, magnesium oxide, tellurium oxide, yttrium oxide, indium oxide, tin oxide, indium oxide tin, and the like. Examples of the composite metal oxide include lithium niobate, potassium niobate, lithium tantalate, and the like. Examples of the metallic compound semiconductor include metal sulfides, such as zinc sulfide and cadmium sulfide, zinc selenide, cadmium selenide, zinc telluride, cadmium telluride, and the like. Examples of the metal include gold and the like.

The inorganic particles may be surface-treated. For example, so-called core shell type inorganic particles in which one kind of inorganic particles are covered with another inorganic component can also be used. Since the titanium oxide has activity induced by light, the titanium oxide is suitably subjected to modification treatment of covering the surface with inorganic components, such as silica and alumina. Moreover, in order to improve the dispersibility to the light absorber base material which is an organic substance, a dispersion assistant having an organic component may be used. The dispersion assistant having an organic component is not particularly limited insofar as it has compatibility with the light absorber base material. The shape of the inorganic particles may be any shape of a spherical shape, an oval shape a flat shape, and a rod shape.

Phantom Base Material

The light propagation characteristics and the acoustic propagation characteristics of the phantom base material are similar to the light propagation characteristics and the acoustic propagation characteristics of human tissues, suitably the acoustic attenuation of adipose tissues.

The phantom base material is preferably a material whose acoustic propagation characteristics are similar to those of a living body and whose acoustic velocity is 800 m/s or more and 2000 m/s or less. For example, a material having an acoustic velocity of 1300 m/s or more and 1700 m/s or less, such as polyurethane gel and natural rubber, is particularly desirable. As the polyurethane gel, the same substances as those mentioned as the polyurethane gel for use in the light absorber base material are mentioned.

In order to approximate the light propagation characteristics of the phantom base material to the light propagation characteristics of human tissues, the absorption coefficient is adjusted by the dispersion of the light absorbing compound. As the light absorbing compound, the same substances as those mentioned as the light absorbing compound for use in the light absorber are mentioned. However, it is not always required to compound two or more kinds of light absorbing compounds in the phantom base material.

To the phantom base material, a light scattering compound may be may added as appropriate, as required. The light scattering compound is added for approximation to the light propagation characteristics of human tissues and can adjust the equivalent scattering coefficient. As the light scattering compound, the same substances as those mentioned as the light scattering compound for use in the light absorber are mentioned.

Acoustic Propagation Characteristics of Phantom Base Material and Light Absorber In the phantom of the present invention, the acoustic propagation characteristics of the light absorber and the phantom base material are different. The acoustic propagation characteristics of the phantom base material and the light absorber are affected by a resin component of the phantom base material and the light absorber base material and are hardly affected by the light absorbing compound and the light scattering compound contained in the phantom base material and the light absorber. Therefore, a method of differentiating the acoustic propagation characteristics of the phantom base material and the light absorber includes, for example, a method of adjusting the density and the acoustic velocity of the resin component of the phantom base material and the light absorber base material to differentiate the acoustic impedance. Specifically, a method of changing the type and the amount of a curing agent to differentiate the molecular weights of both the substances to thereby adjust the density or a method of differentiating the hardness of both the substance to thereby adjust the acoustic velocity is mentioned. Although a difference in the acoustic propagation characteristics between the phantom base material and the light absorber is not particularly limited and the acoustic impedance difference between the phantom base material and the light absorber is suitably 0.1 rayl or more.

Accuracy Control of Apparatus Using Phantom

Hereinafter, an example of applying the phantom of the present invention to the accuracy control of a composite apparatus of a photoacoustic imaging system and an ultrasonic wave diagnostic apparatus is described.

Figure 4:
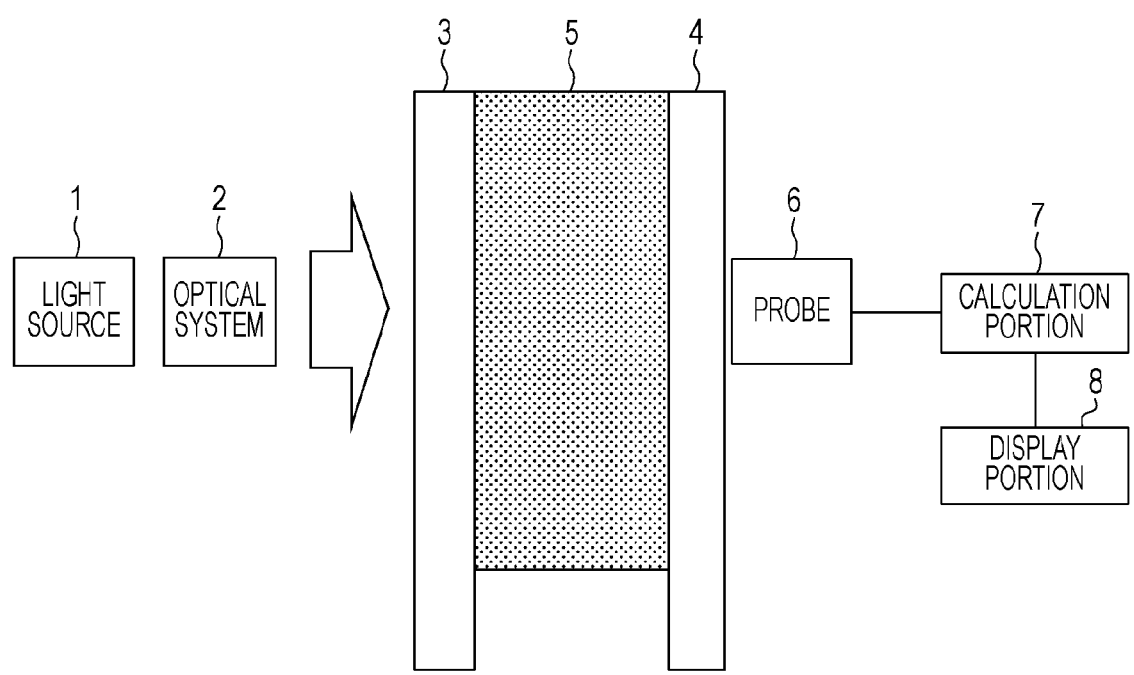
FIG. 4 is a schematic view of an example of a diagnostic apparatus which performs accuracy control using the phantom of the present invention.

FIG. 4 illustrates an example of a composite apparatus of a photoacoustic imaging system and an ultrasonic wave diagnostic apparatus which performs accuracy control using the phantom of the present invention. FIG. 4 includes a light source 1, an optical system 2, a first holding plate 3, a second holding plate 4, a phantom 5, a probe 6, a calculation portion 7, and a display portion 8.

The light source 1 is a light source of emitting a nanosecond order pulsed light at a specific wavelength which irradiates a sample. A feature of the light emitted from the light source 1 selects the wavelength according to the absorption spectra of water, fat, and hemoglobin constituting biological tissues. As one example, the range of 600 to 1100 nm characteristic in the absorption spectra of oxyhemoglobin and deoxyhemoglobin in blood is suitable. As the specific light source 1, a semiconductor laser, tunable laser, and the like which generate different wavelengths can be used and, for example, a titanium sapphire (Ti—S) laser can be used.

The optical system 2 is provided in order to guide the light emitted from the light source 1 to an examination object (phantom 5). The optical system 2 is constituted by an optical fiber and a lens. By the optical system 2, the light emitted from the light source 1 is expanded in such a manner as to irradiate the entire region of the contact surface of the first holding plate 3 and the examination object, and then guided to the surface of the examination object through the first holding plate 3.

It is suitable for the first holding plate 3 and the second holding plate 4 to have high penetrability to the light emitted from the light source 1 and low attenuation properties to acoustic waves. Examples of the materials constituting the holding plates 3 and 4 include glass, polymethyl pentene, polycarbonate, acryl, and the like.

The phantom 5 is held between the first holding plate 3 and the second holding plate 4 to be pressurized and held, and is held at a predetermined distance between the first holding plate 3 and the second holding plate 4. In this case, it is suitably configured so that water or gel is applied to the phantom surface to thereby prevent the formation of air bubbles between the phantom 5 and the holding plates 3 and 4.

The probe 6 has a configuration in which a photoacoustic wave detection probe and an ultrasonic wave transmitting/receiving probe are combined. The photoacoustic wave detection probe is suitably a broadband probe. With respect to the ultrasonic wave transmission frequency, the depth of invasion into human tissues is desirably long. For example, a probe in which a lead zirconate titanate (PZT) is used for a vibrator of the probe, the probe is configured with a 1 mm pitch, the center frequency as a photoacoustic wave detection probe is set to 1 MHz, and the center frequency as an ultrasonic wave probe is set to 6 MHz and the like are mentioned.

The operation portion 7 has a memory relating to the light absorber disposed in the phantom 5 and storing the true values of the optical coefficients, such as the absorption coefficient and the equivalent scattering coefficient. The true value can be calculated by a method described in "Calculation of light propagation characteristics of light absorber" described later. Moreover, an operation unit of comparing a true value with an actually measured value, a correction unit of correcting a measurement error, and an error judging unit of performing error judgment when the true value and the actually measured value are greatly different from each other are provided.

The display portion 8 is a display of displaying the state of the examination object as an image.

A method of performing accuracy control and correction of a photoacoustic imaging system using the phantom of the present invention is described below. For example, it supposed that the actually measured value of the oxygen saturation of the light absorber 12a is 59.6%. When the true value is 55.1%, the error ratio of the oxygen saturation of the light absorber 12a can be calculated as follows, 59.6/55.1=1.08. Similarly, by calculating the oxygen saturation error ratio also about the light absorbers 12b to 12d, the error distribution at each measurement position of the photoacoustic imaging system can be calculated. Moreover, the threshold value for the error judgment is set, and then a function of, judging a case where the error of the true value and the actually measured value is 10% or more as an apparatus error is provided, for example.

A method of perform accuracy control of an ultrasonic wave diagnostic apparatus using the phantom of the present invention is described below. The accuracy control of an ultrasonic wave diagnostic apparatus can be evaluated using the resolution. The resolution is set to the square root (FWHM of PSF: point spread function) of a value obtained by subtracting the square of the diameter of the light absorbers 12a to 12d from the square root of FWHM (full width at half-maximum) of the imaged light absorbers 12a to 12d. The resolution of the ultrasonic wave diagnostic apparatus is about 1 to 1.5 mm when the pitch of probe elements is 1 mm, for example. In this case, a function of judging a case where the resolution reaches 1.5 mm or more as an apparatus error is provided.

EXAMPLES

Hereinafter, examples are described in order to describe the present invention in detail but the present invention is not limited to these examples.

The phantom illustrated in FIG. 1 was produced by a procedure described below. The size of the phantom was 120×120×50 mm. The size of the light absorbers 12a to 12d disposed in the phantom was 1 mm in diameter and 120 mm in length. The light absorbers 12a to 12d were disposed in such a manner as to be able to be detected at a depth position of 25 mm when disposing an apparatus.

(1) Preparation of Light Absorbers 12a to 12d

Two kinds of light absorbing compounds and a light scattering compound were dispersed in a beaker in which polyol was placed, stirred, and then subjected to vacuum defoaming.

As the polyol, a polyether polyol copolymer (Number average molecular weight of 6000) having a molar ratio of ethylene oxide and propylene oxide of 1:1 was used.

As the light absorbing compound, a carbon black pigment and a copper phthalocyanine pigment were used in a proportion of 0.0002% by weight based on polyol with a weight ratio shown in Table 1. As the carbon black pigment and the copper phthalocyanine pigment, a mixture of the pigments and a polyether dispersing agent having affinity with the pigments was used.

As the light scattering compound, titanium oxide (Average particle diameter of 0.21 μm) which was surface-treated with aluminum oxide and hexamethyldisilazane was dispersed in a proportion of 0.24% by weight based on polyol.

Next, xylylene diisocyanate serving as a curing agent was added in a proportion of 40% by weight based on polyol, stirred, and then subjected to vacuum defoaming to thereby prepare a polyurethane gel mixed solution for light absorber.

The polyurethane gel mixed solution for light absorber was poured into a mold, and then heated to be cured. Thereafter, the cured substance was released from the mold to thereby obtain the light absorbers 12a to 12d.

(2) Preparation of Polyurethane Gel Mixed Solution for Phantom Base Material

Only a carbon black pigment was dispersed as a light absorbing compound, and then hexamethylene diisocyanate was added as a curing agent in a proportion of 3.4% by weight based on polyol. A polyurethane gel mixed solution for phantom base material was prepared in the same manner as in the preparation of the light absorbers 12a to 12d, except the process above.

(3) Preparation of Phantom

The light absorbers 12a to 12d were disposed in a mold beforehand, the polyurethane gel mixed solution for phantom base material was poured into a mold, and then heated to be cured. Then, the cured substance was released from the mold to obtain the phantom illustrated in FIG. 1.

Calculation of Light Propagation Characteristics of Light Absorber

Into a 50 mm×50 mm quartz cell having an optical path length of 5 mm, the polyurethane gel mixed solution for light absorber was poured, and then heated at 90° C. for 1 hour to cure the resin to thereby prepare a cell for measuring the light propagation characteristics. The transmittance and the reflectance of the cell were determined using a spectrum photometer (V-670 manufactured by Jasco Corp.). Separately, the refractive index of a sample (10×10×50 mm) which was similarly subjected to resin curing was determined using a refractive coefficient meter (KPR-2000, manufactured by Shimadzu). With respect to these results, optimization of variable setting was performed by Monte Carlo simulation in such a manner that a difference between a measured value and a calculated value was the minimum, and then the equivalent scattering coefficient and the absorption coefficient $\mu_a$ at each wavelength ($\lambda_1$=756 nm, $\lambda_2$=799 nm) were calculated. The determined absorption coefficient $\mu_a$ is shown in Table 1.

Moreover, a parameter S' (oxygen saturation) was determined from Expression (1') using the determined absorption coefficient $\mu_a$ of the light absorber. The results are shown in Table 1.

Calculation of Acoustic Propagation Characteristics

For an ultrasonic wave transducer (transmitting portion) as a probe, "V303" (center frequency of 1 MHz) manufactured by Olympus NDT was used. For a hydrophone (receiving portion), a needle type hydrophone "PAL-1384" manufactured by Precision Acoustics was used. The transducer and the hydrophone were fixed with a jig in the water tank in such a manner that the center of the acoustic axis of the transducer and the center of the acoustic axis of the hydrophone were in agreement with each other. The distance between the transducer and the hydrophone was 40 mm.

The polyurethane gel mixed solution for light absorber or the polyurethane gel mixed solution for phantom base material was cured to prepare a sheet of a size of 100 mm×100 mm and 5 mm in thickness or 10 mm in thickness. The sheet was fixed between the transducer and the hydrophone using a jig in such a manner that the incidence angle of an ultrasonic wave signal to the sheet was 0°. A sign wave (Transmission voltage of 100 V) of one cycle was transmitted from the transducer using a function generator (AFG3022, manufactured by Tectronix), and then the received voltage value of the hydrophone when disposing each sheet was calculated using an oscilloscope (TDS 3012C, manufactured by Tectronix). With respect to the acoustic velocity, a difference in the received wave arrival time between a case where the sheet was disposed in the measurement system and a case where the sheet was not disposed in the measurement system was determined using an oscilloscope. The acoustic attenuation was determined from the following expression. The results are shown in Table 2.

[Math. 5]

$$\text{Acoustic attenuation per 1 cm/1 MHz (dB/cm/MHz)} = 20 \times \log\left[\frac{\text{Received sound pressure when disposing 10 mm thick sheet}}{\text{Received sound pressure when disposing 5 mm thick sheet}}\right] \times \frac{10 \text{ (mm)}}{5 \text{ (mm)}}$$

TABLE 1

| Light absorber | Carbon black pigment/Copper phthalocyanine pigment (weight ratio) | $\mu_a$ [756 mm] (mm$^{-1}$) | $\mu_a$ [797 mm] (mm$^{-1}$) | Oxygen saturation (%) |
|---|---|---|---|---|
| 12a | 0.5 | 0.0328 | 0.0258 | 55.07 |
| 12b | 0.8 | 0.0304 | 0.0252 | 60.22 |
| 12c | 1.2 | 0.0284 | 0.0248 | 65.06 |
| 12d | 1.9 | 0.0266 | 0.0246 | 70.13 |

TABLE 2

| | Acoustic velocity [m/s] | Density | Acoustic impedance [rayl] | Acoustic attenuation [dB/cm/MHz] |
|---|---|---|---|---|
| Phantom base material | 1393.9 | 1.03 | 1.44 | 0.47 |
| Light absorber | 1508.3 | 1.08 | 1.63 | 1.08 |

The absorption coefficient $\mu_a$ of the red corpuscles at the wavelength of 797 nm is about 0.02 mm$^{-1}$ and, as shown in Table 1, the absorption coefficient at the wavelength of 797 nm of the light absorbers 12a to 12d is a value close to 0.02 mm$^{-1}$. Therefore, the phantom of this example is a phantom having light absorbers suitable for detecting hemoglobin. Moreover, as shown in Table 1, light absorbers whose oxygen saturation was adjusted at 5% intervals were obtained by adjusting the dispersion weight ratio of the carbon black pigment and the copper phthalocyanine pigment.

Moreover, as shown in Table 2, the phantom base material in this example achieved the acoustic propagation characteristics which were almost equal to those of human tissues. Since different curing agents were used in different proportions in the light absorbers and the phantom base material, and the acoustic velocity was adjusted by increasing the hardness of the light absorbers to be higher than the hardness of the phantom base material, the acoustic impedance of the light absorbers was also higher than the acoustic impedance of phantom base material. The carbon black pigment and the copper phthalocyanine pigment did not affect the acoustic characteristics. Therefore, by the use of the phantom of this example, the accuracy control of the function evaluation of the oxygen saturation and the accuracy control of the shape evaluation using ultrasonic waves can be simultaneously performed.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-108701, filed May 23, 2013 which is hereby incorporated by reference herein in its entirety.

The invention claimed is:

1. A phantom, comprising:
a light absorber in a phantom base material, wherein
the light absorber approximates a light absorption coefficient ratio at two or more wavelengths to that of biological materials, and
acoustic propagation characteristics of the phantom base material and the light absorber are different from each other,
wherein the light absorber contains two or more kinds of light absorbing compounds in a light absorber base material, absorption coefficient ratios $\mu[\lambda_2]/\mu[\lambda_1]$ of the light absorbing compounds at arbitrary two wavelengths $\lambda_1$ and $\lambda_2$ ($\lambda_1<\lambda_2$) of 600 nm or more and 1100 nm or less are different from each other, and a parameter S calculated from the following equation (1) is 0 or more and 100 or less, and
wherein a coefficient of linear expansion of the light absorber base material is 100 ppm/K or more and 1000 ppm/K or less, $$S = \frac{P' \cdot Hb[\lambda_1] - Hb[\lambda_2]}{(HbO_2[\lambda_2] - Hb[\lambda_2]) - P' \cdot (HbO_2[\lambda_1] - Hb[\lambda_1])} \cdot 100 \quad \text{equation (1)}$$

wherein $HbO_2[\lambda_1]$ indicates an absorption coefficient of oxyhemoglobin at the wavelength $\lambda_1$, $HbO_2[\lambda_2]$ indicates an absorption coefficient of oxyhemoglobin at the wavelength $\lambda_2$, $Hb[\lambda_1]$ indicates an absorption coefficient of deoxyhemoglobin at the wavelength $\lambda_1$, $Hb[\lambda_2]$ indicates an absorption coefficient of deoxyhemoglobin at the wavelength $\lambda_2$, and P' indicates a ratio ($P_{\lambda_2}/P_{\lambda_1}$) of a photoacoustic signal intensity $P_{\lambda_2}$ obtained by irradiation with light of the wavelength $\lambda_2$ to a photoacoustic signal intensity $P_{\lambda_1}$ obtained by irradiation with light of the wavelength $\lambda_1$.

2. A phantom, comprising:
a light absorber in a phantom base material, wherein
the light absorber approximates a light absorption coefficient ratio at two or more wavelengths to that of biological materials, and
acoustic propagation characteristics of the phantom base material and the light absorber are different from each other,
wherein the light absorber contains two or more kinds of light absorbing compounds in a light absorber base material, absorption coefficient ratios $\mu[\lambda_2]/\mu[\lambda_1]$ of the light absorbing compounds at arbitrary two wavelengths $\lambda_1$ and $\lambda_2$ ($\lambda_1<\lambda_2$) of 600 nm or more and 1100 nm or less are different from each other.

3. The phantom according to claim 2, wherein the light absorber contains at least one light absorbing compound in which the absorption coefficient ratio $\mu[\lambda_2]/\mu[\lambda_1]$ satisfies one of the following equation (2) or equation (3), $$S_{min} \geq \frac{(\mu[\lambda_2]/\mu[\lambda_1]) \cdot Hb[\lambda_1] - Hb[\lambda_2]}{(HbO_2[\lambda_2] - Hb[\lambda_2]) - (\mu[\lambda_2]/\mu[\lambda_1]) \cdot (HbO_2[\lambda_1] - Hb[\lambda_1])} \cdot 100 \quad \text{Equation (2)}$$

$$S_{max} \leq \frac{(\mu[\lambda_2]/\mu[\lambda_1]) \cdot Hb[\lambda_1] - Hb[\lambda_2]}{(HbO_2[\lambda_2] - Hb[\lambda_2]) - (\mu[\lambda_2]/\mu[\lambda_1]) \cdot (HbO_2[\lambda_1] - Hb[\lambda_1])} \cdot 100 \quad \text{Equation (3)}$$

wherein $S_{min}$ indicates a lower limit of the parameter S, $S_{max}$ indicates an upper limit of the parameter S, $HbO_2[\lambda_1]$ indicates an absorption coefficient of oxyhemoglobin at the wavelength $\lambda_1$, $HbO_2[\lambda_2]$ indicates an absorption coefficient of oxyhemoglobin at the wavelength $\lambda_2$, $Hb[\lambda_1]$ indicates an absorption coefficient of deoxyhemoglobin at the wavelength $\lambda_1$, $Hb[\lambda_2]$ indicates an absorption coefficient of deoxyhemoglobin at the wavelength $\lambda_2$, $\mu[\lambda_1]$ indicates an absorption coefficient of the light absorbing compound at the wavelength $\lambda_1$, and $\mu[\lambda_2]$ indicates an absorption coefficient of the light absorbing compound at the wavelength $\lambda_2$.

4. The phantom according to claim 3, wherein the light absorber further contains at least one light absorbing compound in which the absorption coefficient ratio $\mu[\lambda_2]/\mu[\lambda_1]$ satisfies the other one of the equation (2) or equation (3).

5. The phantom according to claim 2, wherein an acoustic velocity in the light absorber base material is 1300 m/s or more and 1700 m/s or less.

6. The phantom according to claim 2, wherein the light absorber base material contains a polymer material.

7. The phantom according to claim 6, wherein the light absorber base material is a polyurethane gel.

8. The phantom according to claim 2, wherein at least one of the light absorbing compounds is a phthalocyanine compound.

9. The phantom according to claim 8, wherein the light absorber contains the phthalocyanine compound in a proportion of 0.000001% by weight or more and 0.1% by weight or less.

10. The phantom according to claim 2, wherein at least one of the light absorbing compounds is carbon black.

11. The phantom according to claim 2, wherein the arbitrary two wavelengths $\lambda_1$ and $\lambda_2$ are $\lambda_1$=756 nm and $\lambda_2$=799 nm.

12. The phantom according to claim 2, wherein the phantom base material and the light absorber approximate light propagation characteristics and acoustic propagation characteristics to those of human materials.

13. The phantom according to claim 12, wherein the light propagation characteristics are light scattering properties or light absorbability.

14. The phantom according to claim 12, wherein the light propagation characteristics are light propagation characteristics at a wavelength of 600 to 1100 nm.

15. The phantom according to claim 2, wherein the acoustic propagation characteristics are acoustic impedance.

16. The phantom according to claim 15, wherein a difference in the acoustic impedance between the phantom base material and the light absorber is 0.1 rayl or more.

17. The phantom according to claim 2, wherein the acoustic propagation characteristics refer to acoustic attenuation.

18. The phantom according to claim 2, wherein the acoustic propagation characteristics are acoustic propagation characteristics at a frequency of 0.5 to 10 MHz.

19. The phantom according to claim 2, wherein the biological materials is hemoglobin.

20. The phantom according to claim 2, wherein the phantom base material contains a polyurethane gel.

* * * * *